United States Patent [19]

Pennig et al.

[11] Patent Number: 4,917,111

[45] Date of Patent: Apr. 17, 1990

[54] INSTRUMENT FOR AIMING AND HOLE FORMING FOR IMPLANTATION OF LOCKING NAILS OF THE LIKE

[76] Inventors: Dietmar Pennig; Erwin Brug; Hans E. Harder, all of Pfizer Inc. 235 E. 42nd St., New York, N.Y. 10017-5755

[21] Appl. No.: 109,139

[22] Filed: Oct. 15, 1987

[51] Int. Cl.⁴ ............................................. A61F 5/04
[52] U.S. Cl. ..................................................... 606/97
[58] Field of Search ....... 128/92 VY, 92 VD, 92 VT, 128/92 VZ; 378/162, 164, 205

[56] References Cited

U.S. PATENT DOCUMENTS

| | | | |
|---|---|---|---|
| 2,500,370 | 3/1950 | McKibbin | 128/92 VD |
| 2,531,734 | 11/1950 | Hopkins | 128/92 VD |
| 2,607,339 | 8/1952 | Price | 128/92 VD |
| 4,037,592 | 7/1977 | Kronner | 128/92 VD |
| 4,230,117 | 10/1980 | Anichkov | 378/162 |
| 4,541,424 | 9/1985 | Grosse et al. | 128/92 VD |
| 4,750,487 | 6/1988 | Zanetti | 378/162 |

FOREIGN PATENT DOCUMENTS 0201737 4/1986 European Pat. Off. .

Primary Examiner—Robert A. Hafer
Assistant Examiner—Michael Brown
Attorney, Agent, or Firm—Peter C. Richardson; Lawrence C. Akers; Elizabeth O. Slade

[57] ABSTRACT

Surgical instrument for aiming and hole-forming purposes for use for example in the implantation of locking nails or the like in bones, the instrument includes an elongated shank and having a gripping portion at one end thereof and an aiming portion at the other end thereof, the aiming portion including a guide member made of a material relatively transparent to X-rays, the guide member having a bore therethrough adapted to slidingly receive an elongated hole-forming tool and having aiming elements located in different planes, the guiding bore being dimensioned for the guidance of a wire-like piercing tool, and the aiming elements being located around the guiding bore in axially spaced planes such that images of the aiming elements coincide on an image screen when the axis of the guiding bore coincides with the beam direction of said X-rays.

9 Claims, 1 Drawing Sheet

U.S. Patent     Apr. 17, 1990     4,917,111
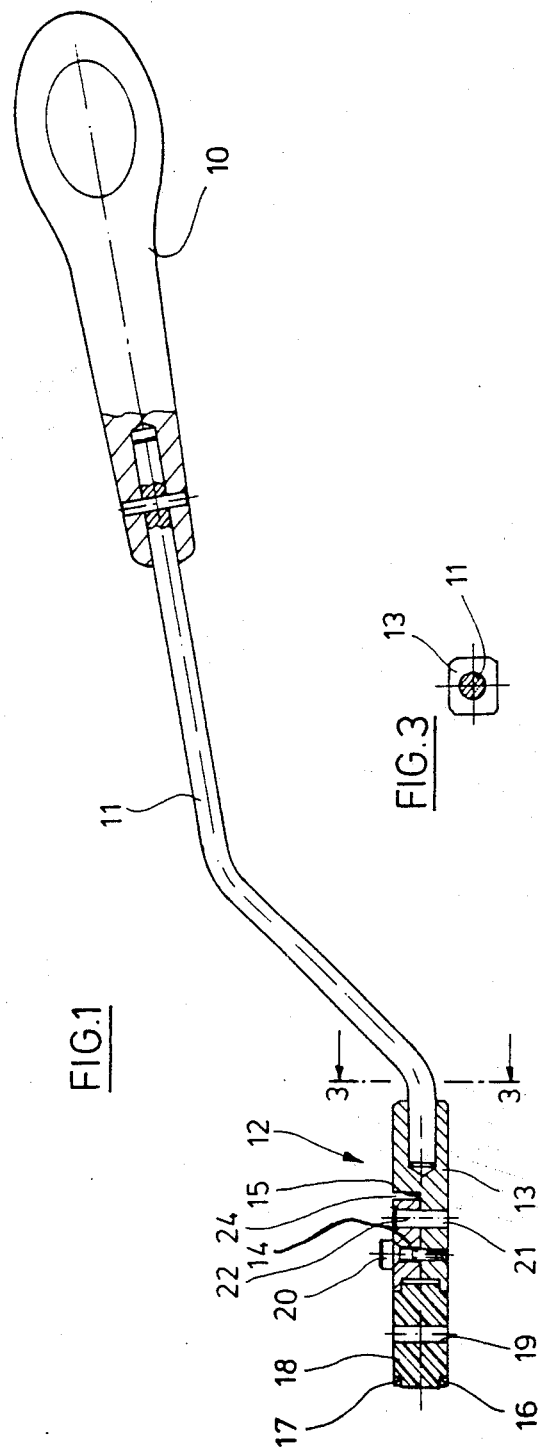
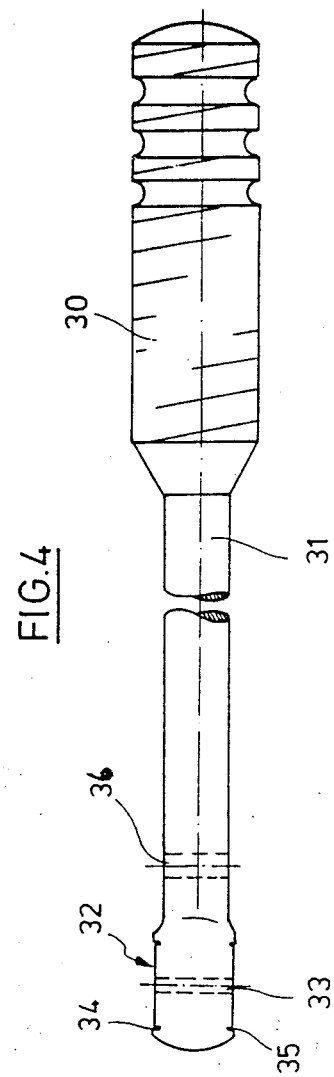
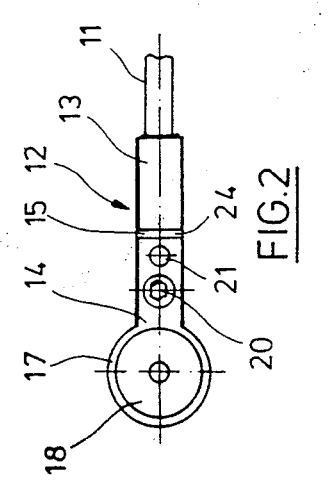

INSTRUMENT FOR AIMING AND HOLE FORMING FOR IMPLANTATION OF LOCKING NAILS OF THE LIKE

BACKGROUND OF THE INVENTION

The invention refers to a surgical instrument for aiming and hole forming purposes in connection with the implantation of locking nails or the like in bones.

As known, locking nails are bone nails which are introduced in the bone canal. The locking nails have transverse bores so that the locking nails can be fixed in the bone canal by bone screws inserted in transverse bores in the bones and through the transverse bores in the locking nail. By this the locking nails can be secured in the bone with respect to the axial and the torsional direction. Before placing the bone screws through the transverse bores in the locking nail corresponding bores must be made in the bone. It is clear that these bores must be coaxial with the transverse bores in the locking nail. However, it is not possible to determine the exact position of the transverse bores without specific means. Thus, aiming means are necessary for the application of locking nails. Most known aiming devices require a high energy radiation source, e.g. an X-ray source and receiving means and an image converter. In a known aiming device a drill sleeve serving for the guidance of the ddrill bit is attached to the housing or the frame of the X-ray source. Since the aiming device must be accommodated the different X-ray devices of the aiming device have to be designed in a different manner. This leads to relatively high costs.

Another known aiming device uses the proximal end of the locking nail as reference in order to determine the axial position of the transverse bores. The distance of the transverse bores from the proximal end is predetermined. Thus, it is only necessary to determine the axis of the transverse bores by means of the aiming device. A further aiming device can be used freehand by the surgeon (German utility model 84 17 428). A driving motor is accommodated in the aiming device and the chuck for retaining the tool, e.g. a drill bit, is transparent to X-rays. In this embodiment the drill bit is used as aiming means making use of the fact that the drill bit will appear on the image screen approximately as a point only if it extends approximately parallel to the beam direction. It is further necessary that the beam direction is coincident with the axis of the transverse bores. This can be determined by the image of the transverse bores. These are only circular when this coincidence is reached.

Finally, an aiming instrument is known including a drill sleeve attached to a gripping portion, the aiming means being connected to said drill sleeve in a defined position, the position of said aiming means between a radiation source and a radiation receiver being adapted to be illustrated on the screen of a converter (EPO application 0 201 737). Such an instrument also can be used freehand. The aiming means separated from the drilling sleeve has the advantage that a control and a correction of the aiming operation can be made also during the drilling operation. The known aiming device, however, requires a separate aiming element for the precise determination of the drilling axis, the aiming element being received by the drilling sleeve. The aiming element is defined by a pin made of material transparent to X-rays having a light-tight point or tip. By means of the aiming means and the aiming pin the drilling sleeve can be brought into an exact position against the bone. After a further adjustment by the aiming means a hole is formed by the drilling tool inserted in the drilling sleeve. The known aiming instrument, thus, requires two subsequent aiming operations which necessitate a certain time expense.

SUMMARY OF THE INVENTION

It is therefore an object of the present invention to provide for a surgical aiming instrument for the aiming and forming of holes for the implantation of locking nails or the like which can be easily handled and allows a more simple formation of the holes or bores.

This problem is solved by the apparatus and method of the invention.

In the aiming instrument according to the invention a guide member is made of a material transparent to X-rays. The guide member is provided with a guiding bore adapted to slidingly guide a wire-like piercing tool. Further, aiming portions impervious to X-rays are associated with the guide member, the aiming portions being arranged in spaced planes extending perpendicularly to the axis of the guiding bore, the images of the aiming portions arriving at a coincident position on the screen if the guiding bore is aligned with the beam direction of the X-rays.

In the invention it has been recognized that it is possible without difficulties to pierce the lateral cortikalis by a suitable piercing tool, the cortikalis being pierced upon a small number of strokes against the piercing tool. The hole made in such a manner is precisely aligned with the axis of the transverse bore in the locking nail. This is achieved by means of the aiming portions which indicate on the screen of the image converter when the axis of the guiding bore aligns with the axis of the transverse bore. In a subsequent operation the hole made by the piercing tool can be enlarged by a drilling operation. Concurrently in the drilling operation a hole can be formed in the opposite cortikalis.

Piercing tools suitable for the instrument according to the invention are known, e.g. so-called Steinmann pins. Such pins are used for instance to exert a tensional force on bone fracture segments or to attach a device to a bone externally.

The alignment of the tip of the piercing tool in the guiding bore with the axis of the transverse bore in the locking nail can be achieved by observing the image on the image converter screen. This can be carried out such that first only the tip of the piercing tool is placed at the precise location. This makes necessary that the piercing tool is inclined to the axis of the transverse bore. Thereafter the instrument is turned until the aiming portions coincidently appear on the image screen. This indicates that the axis of the piercing tool is aligned with the axis of the transverse bore in the locking nail. With a single or a plurality of strokes with a hammer or another striking tool on the piercing instrument a hole is obtained aligned with the transverse bore.

The aiming portions can be defined in a different manner. One embodiment provides segments arranged about the axis of the guiding bore. Preferably, the segments are arranged in a circle around the guiding bore, preferably coaxial to the guiding bore. In another embodiment the aiming portions can be defined by an annulus surrounding the guiding bore.

The guide member is preferably formed of plastic material. Plastic material is transparent to X-rays. In order to retain the guide member of plastic material the aiming portions may serve as retaining means for the guide member. Since the guiding bore in the guide member is subjected to wear it may occur that the guide member must be replaced by a fresh one from time to time. For this an aiming portion can be releasably attached to the shank.

An alternative embodiment provides that the gripping portion, the shank and the guide member are integrally molded of plastic material. Such a structure can be easily manufactured without substantial expense by suitable molding techniques. In case the guiding bore is enlarged in its diameter due to frequent use this instrument can be thrown away and replaced by another one.

The instrument according to the invention can be provided with a slot or the like in spaced relation to the guiding bore, the slot extending transversely to the axis of the guiding bore. Such a slot or groove can be observed on the image converter screen with the end portions thereof if the instrument is not precisely adjusted. Depending upon whether the slot can be seen at the top or the lower side the surgeon knows to which side the instrument must be turned in order to obtain the desired alignment.

Usually locking nails have a pairwise arrangement of transverse bores. In order to avoid a further aiming operation which requires a displacement of the X-ray device a further bore can be provided spaced to the guiding bore, the further bore being adapted to receive a drilling sleeve the axis thereof being parallel to the axis of the guiding bore. The formation of the first hole takes place as described above. The piercing tool is pierced through the lateral cortikalis and fixed in the opposite cortikalis. By this the axis of the drilling sleeve in the further bore has the same distance to the piercing tool as the second transverse bore to the first one. It is only necessary then to rotate the instrument about the piercing tool in order to align the axis of the drill bit with the axis of the second transverse bore.

DETAILED DESCRIPTION OF THE INVENTION

The invention will be described hereinafter with drawings showing preferred embodiments.

FIG. 1 is a side view partially in cross section of an aiming instrument according to the invention.

FIG. 2 is a view of a portion of the instrument shown in FIG. 1.

FIG. 3 is a cross section through the instrument according to FIG. 1 along line 3—3.

FIG. 4 is a schematic view of an alternative embodiment according to the invention.

The instrument shown in FIG. 1 includes a gripping portion 10, a cranked shaft 11 connected to the gripping portion and a guiding and aiming device 12 attached to the opposite end of the shank 11. The latter device includes two plates 13, 14, plate 13 being secured to shank 11. Plate 13 includes a lowered flat surface 15 upon which plate 14 can be laid, the upper surface of plate 14 being approximately at the same level as the back portion of plate 13, as can be seen in FIG. 1. A circular ring member 16 is externally formed on plate 13. A further ring member 17 is so formed on plate 14. The inner and outer diameters of the rings 16, 17 are equal. It can be seen that the ring members 16, 17 are seated in circular grooves at the edge of the substantially circular guide member 18. Thus, the ring members 16, 17 form a socket or retaining means for the guide member 18. The guide member 18 is made of plastic material, e.g. of polyamide and includes a central guiding bore 19. Ring members 16, 17 are made of metal.

The plates 13, 14 are tightened against each other by means of a screw fastener 20. A fitting pin 21 attached to plate 13 is fittingly received by a bore 22 in plate 14.

The guiding bore 19 is dimensioned such that a piercing tool, e.g. a Steinmann pin or the like can be slidingly received. However, the pin is retained in bore 19 by sufficient friction so that the pin does not drop out of the instrument during its handling. In a surgical operation first an alignment between a transverse bore of the locking nail and the radiation of an X-ray source is carried out such that the transverse bore appears on the image screen in its circular form. This means that the axis of the transverse bore is substantially aligned to the beam axis of the radiation. Thereafter a pin retained in the guiding bore 19 is positioned with its tip or point such that the tip is on the axis of the transverse bore of the locking nail. In this operation the pin is engaging the lateral cortikalis while the axis of the pin is inclined relative to the axis of the transverse bore in order to allow a precise observation of the tip. After the precise position of the tip has been found the instrument is moved using the tip engaging the cortikalis as turning point. This movement is made as long as the ring members 16, 17 which are concentrically arranged around the guiding bore are coincidently shown on the converter screen (the remaining apparatuses and the locking nail and the instruments for implantating the locking nails are not shown since they belong to the prior art, e.g. EPO application 0 201 737).

After the desired adjustment has been made the pin is driven in the associated cortikalis by one or a plurality of strokes against the pin. Thereafter the hole made by the pin is drilled by means of a drill bit by which a hole can be drilled also in the opposite cortikalis, the transverse bore in the locking nail serving as guiding means for drilling the opposite hole.

The plates 13, 14 leave a groove 24. By observing the position of the groove the surgeon can recognize whether the instrument must be turned to the left or the right side in order to bring the ring members 16, 17 to their coincidence.

If the guiding bore 19 is enlarged too much the plates 13, 14 are separated from each other. A fresh guide member 18 can be placed between ring members 16, 17.

The instrument shown in FIG. 4 includes also a gripping portion 30, a shank 31 and guiding and aiming means 32. The portions 30, 31 and 32 are integrally molded of plastic material. A guiding bore 33 in device 32 corresponds to the guiding bore 19 of FIG. 1. Metal ring members 34, 35 are embedded in the head of device 32 corresponding to the metal ring members 16, 17 according to FIG. 1. The operation of the instrument of FIG. 4 corresponds to that of FIG. 1. Additionally, a further bore 36 is provided spaced from the guiding bore 33. The further bore serves for the receipt of a drilling sleeve. The distance between bores 33, 36 corresponds to the distance of transverse bores in the locking nail. The instrument according to FIG. 4 can be fixed in its position by means of a piercing tool by piercing the piercing tool through the lateral cortikalis and through the transverse bore of the locking nail. The piercing tool is partially driven into the opposite cortikalis. Thereafter the instrument can be turned about the pin or the piercing tool until the axis of the drilling sleeve or the bore 34 is aligned with the axis of the second transverse bore of the locking nail.

We claim:

1. Apparatus for aiming and hole forming purposes for the implantation of locking nails or the like in bones, said apparatus comprising:
  (A) an elongated shank having a gripping portion to be gripped by a hand at one end of said shank and
  (B) an aiming portion at the other end of said shank, said aiming portion including:
     (1) a guide member made of a material relatively transparent to X-rays, said guide member having
        (a) a guiding bore therethrough and
        (b) a first aiming element and a second aiming element each located in a different plane, said guiding bore being dimensioned for the guidance of a bone piercing tool which is to be used in conjunction with said apparatus in order to pierce a bone of a patient, and said first aiming element and said second aiming element being formed from a material relatively impervious to X-rays and being located around said guiding bore in axially spaced apart planes such that when a beam of X-rays is incident upon said aiming elements, X-ray images of said aiming elements coincidentally appear on an image screen which is to be used in conjunction with said apparatus and which is placed downstream with respect to said X-rays when the axis of said guiding bore coincides with the direction of said beam of incident X-rays.

2. The apparatus of claim 1, wherein said aiming elements comprise elements which are selected from the group consisting of axially spaced apart rings encompassing said guiding bore and axially spaced apart ring segments encompassing said guiding bore.

3. The apparatus of claim 2, wherein the rings serve as retaining means for the guide member.

4. The apparatus of claim 3, wherein at least one ring member is releasably secured to said shank.

5. The apparatus of claim 1, wherein the guide member is made of plastic material and the aiming elements are received in a depression of the guide member or are embedded therein.

6. The apparatus of claim 1, wherein the gripping portion, the shank and the guide member are integrally molded of plastic material.

7. The apparatus of claim 1, wherein a slot is provided located in spaced relation to the guiding bore and extending transversely thereto.

8. The apparatus of claim 1, wherein a further throughbore is provided at a distance from the guiding bore, said further throughbore being provided for the receipt of a drill sleeve, the axis of the further throughbore extending parallel to the axis of said guiding bore.

9. Apparatus for precise placement of at least two holes in a bone comprising the apparatus of claim 1 and including also a piercing tool located within said guide member.

* * * * *